United States Patent [19]

McMillan

[11] Plant 4,467

[45] Oct. 23, 1979

[54] AFRICAN VIOLET NAMED LIGHT MARTA

[75] Inventor: Edward A. McMillan, Oregon City, Oreg.

[73] Assignee: Pan-American Plant Company, West Chicago, Ill.

[21] Appl. No.: 958,688

[22] Filed: Nov. 8, 1978

[51] Int. Cl.[2] ..... A01H 5/00

[52] U.S. Cl. ..... Plt./69

[58] Field of Search ..... Plt./69

*Primary Examiner*—Robert E. Bagwill
*Assistant Examiner*—James R. Feyrer
*Attorney, Agent, or Firm*—Chas. W. Rummler

[57] ABSTRACT

A new African violet variety for potted plant culture particularly distinguished by the light lavender color of its flowers. Otherwise this cultivar exhibits substantially the same morphological characteristics of the variety "Marta" (U.S. Plant Pat. No. 3,610), of which the variety is a sport.

1 Drawing Figure

BACKGROUND OF THE NEW PLANT

This new variety of African violet plant was discovered by me in 1976, at Clackamas, Oreg., among a field of the violet variety "Marta" (U.S. Plant Pat. No. 3,610) being grown under glass for commercial purposes. The very light lavender color of the flower prompted me to reproduce this sport by cuttings, which I did at Clackamas, Oreg., and subsequent propagations, by both cuttings and meristem culture, through successive generations has shown that the novel characteristics of this new plant hold true from generation to generation and appear to be firmly fixed. This new plant is now being propagated at West Chicago, Ill. and at Parrish, Fla.

DESCRIPTION OF THE DRAWING

My new variety of African violet is illustrated by the accompanying full color photographic drawing which shows the color characteristics of the flowers, the color rendition being as nearly true as it is reasonably possible to obtain by conventional professional photographic procedures.

DESCRIPTION OF THE NEW PLANT

The following is a detailed description of my new African violet plant with color description according to the R.H.S. Colour Chart (RHS) published by The Royal Horticultural Society of London, England, in collaboration with The British Colour Council.

THE PLANT

Origin: Sport

Parentage: The violet variety "Marta" (U.S. Plant Pat. No. 3,610).

Classification:

*Botanic.*—*Saintpaulia ionantha.*

*Commercial.*—African Violet.

Form: Compact potted plant (rosette arrangement).

Height: 8.5 to 10 cm.

Growth: Vigorous and condensed with strong petioles which are inclined to spread horizontally and with sturdy, upright flower peduncles.

Foliage: Quantity — abundant.

*Size of leaf.*—6.2 to 9.9 cm. long and 4.5 to 6.9 cm. wide.

*Shape of Leaf.*—Ovate with crenate margins.

*Texture.*—Leathery and tomentose.

*Aspect.*—Pubsecent.

*Color.*—Upper side — 147A. Under side — 157A.

*Petioles.*—1.6 to 4.5 cm.

*Ribs and veins.*—Pinnate and very pronounced on the under side of the leaf.

THE BUD

Form: Globular (ovoid) becoming urn-shaped as bud opens.

Size: 5 to 7 mm. in diameter; 6 to 9 mm. in depth.

Opening Rate: The bud opens slowly with five weeks from visible bud to opening of the flower.

Color: When sepals first divide — 76D. When petals begin to unfurl — 76C.

Sepals: Hooded over the bud for a very short time.

*Form.*—Spear-shaped and upstanding.

*Color.*—Inside — 148A. Outside — 147B.

Calyx: Funnel-shaped and synsepalous.

*Splitting.*—Calyx splits to a star shape.

*Aspect.*—Smooth on inside and hairy on the outside.

Peduncle: 5.0 to 6.4 cm. long.

*Aspect.*—Hairy.

*Strength.*—Erect.

*Color.*—183A.

THE FLOWER

Blooming habit: Profuse and recurrent the year around.

Size of flower: Large, about 3.75 cm. in diameter.

Shape of flower: Very open cup-shape when bloom first opens, becoming flat as bloom matures.

Borne: As a cyme.

Petalage: Number of petals — five, three being larger than the remaining two.

*Arrangement.*—Sympetalous.

*Form.*—Orbicular with bilateral symmetry and undulated margins.

*Texture.*—Soft and velvety.

*Aspect.*—Glittery on upper side and satiny on under side.

Color:

| | | Immature Bloom | Mature Bloom |
|---|---|---|---|
| 3 large petals - | Upper Side | 76B, 76C | 75C, 75D |
| | Reverse Side | 76D | 75D |
| 2 smaller petals - | Upper side | 82D | 77D |

-continued

| | Immature Bloom | Mature Bloom |
|---|---|---|
| Reverse side | 82D | 75B |

Tonality at 2 Meters: 75B and 75C.

Peduncle: Sturdy and upright.

*Length.*—5.0 to 6.4 cm.

*Color.*—183A.

Effect of Weather: Flowering is suppressed and color fades in hot weather. This plant thrives in 80% to 90% humidity.

Fragrance: Slight.

Persistence: Flowers hang on and dry.

Lasting quality: 14 to 18 days for the fully opened flower. This plant is not recommended for cut flowers.

REPRODUCTIVE ORGANS

Stamens: Arrangement — basifixed.

*Anthers.*—2 in number, each composed of 2 anther cells. Length: 1.5 to 2.5 mm.

*Filaments,*— 2 to 3 mm. long. Color: 78B.

*Pollen.*—Color — white.

Pistils: One only.

*Style.*—7 to 9 mm. long.

*Stigma.*—Color —78B.

*Ovaries.*—Superior and tomentose.

This variety of African violet is very similar to its parent "Marta" (U.S. Plant Pat. No. 3,610) in most of its morphological characteristics, the principal distinction of the new plant being the very light lavender coloration of its flowers when compared with those of its parent "Marta".

I claim:

1. A new cultivar of African violet plant substantially as herein shown and described, characterized by the unique light lavender coloration of its flowers.

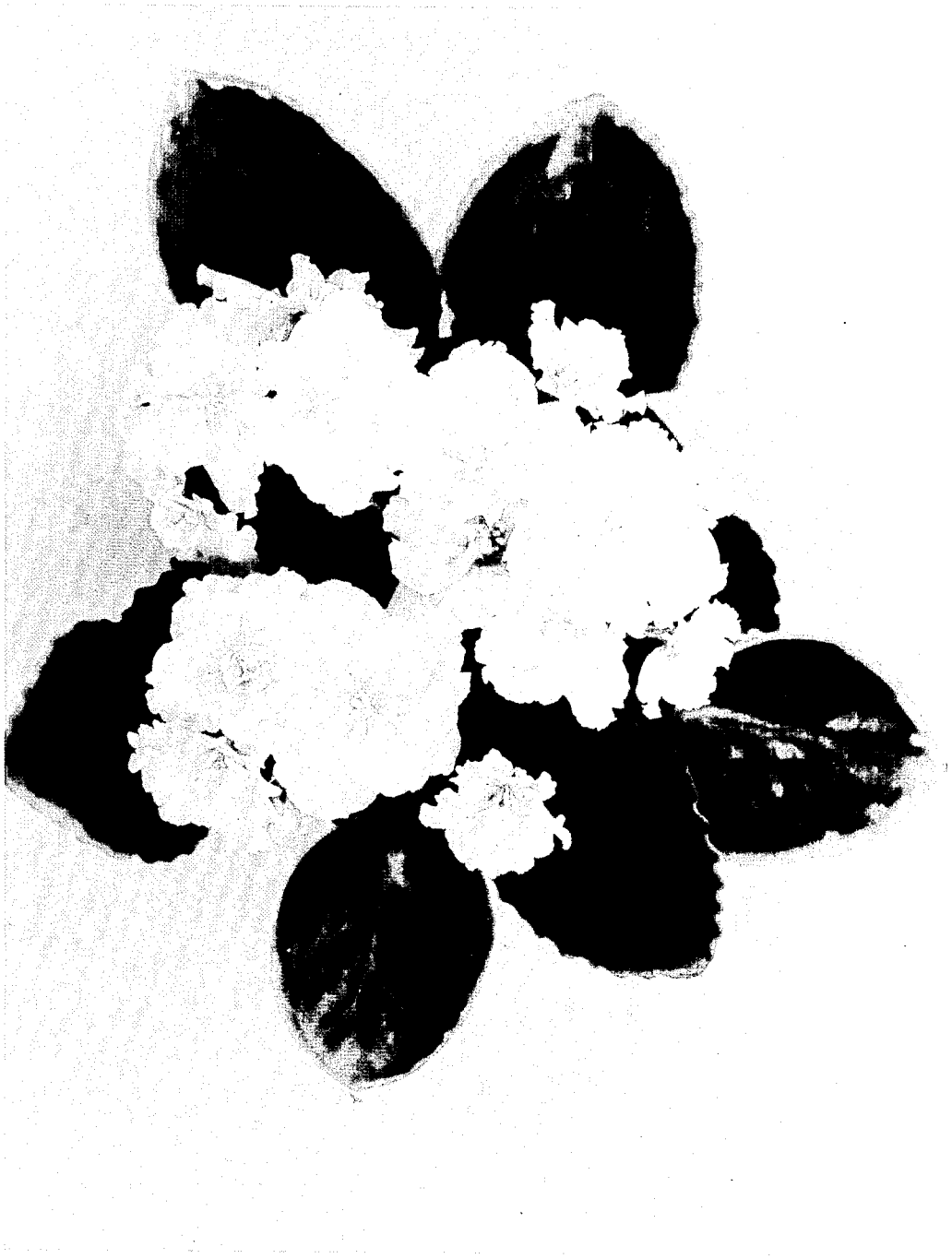

* * * * *